(12) United States Patent
Yoo

(10) Patent No.: US 8,314,051 B2
(45) Date of Patent: Nov. 20, 2012

(54) METHOD OF PREPARING 1-METHYLCYCLOPROPENE AND APPLYING THE SAME TO PLANTS

(75) Inventor: Sang-Ku Yoo, Gwacheon-si (KR)

(73) Assignee: Erum Biotechnologies Inc., Siheung-Si, Gyeonggi-Do (KR)

( * ) Notice: Subject to any disclaimer, the term of this patent is extended or adjusted under 35 U.S.C. 154(b) by 482 days.

(21) Appl. No.: 12/553,640

(22) Filed: Sep. 3, 2009

(65) Prior Publication Data

US 2010/0076242 A1  Mar. 25, 2010

(30) Foreign Application Priority Data

Sep. 25, 2008  (KR) .................. 10-2008-0093959

(51) Int. Cl.
*A01N 27/00* (2006.01)
*A01N 43/10* (2006.01)
*A01N 43/84* (2006.01)
*A01N 55/08* (2006.01)
*A01N 65/00* (2009.01)
*A01N 41/02* (2006.01)
*A61K 31/255* (2006.01)
*A61K 31/695* (2006.01)

(52) U.S. Cl. ........ 504/357; 504/289; 504/224; 504/189; 504/193; 514/63; 514/517

(58) Field of Classification Search .................. 504/357, 504/289, 224, 189, 193; 514/63, 517
See application file for complete search history.

(56) References Cited

U.S. PATENT DOCUMENTS 5,518,988 A  5/1996  Sisler et al.

(Continued)

FOREIGN PATENT DOCUMENTS

KR  10-0823872 A  4/2008

OTHER PUBLICATIONS http://dictionary.reference.com/browse/in+situ; 2011; Dictionary.com Unabridged; Random House Dictionary, Random House, Inc. (downloaded Dec. 22, 2011).*

(Continued)

*Primary Examiner* — Richard Schnizer
*Assistant Examiner* — Jane C Oswecki
(74) *Attorney, Agent, or Firm* — Birch Stewart Kolasch & Birch, LLP

(57) ABSTRACT

Disclosed is a method for directly preparing in situ 1-methylcyclopropene which inhibits the action of ethylene of accelerating the ripening process of plants, which comprises reacting a predetermined 1-methylcyclopropene precursor represented by the following Formula 2 or 3 with a base or fluoride anion material, and applying the 1-methylcyclopropene to plants:

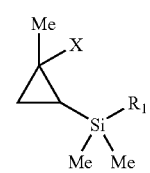

(2)

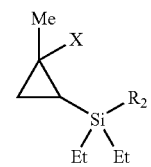

(3)

wherein Me, Et, $R_1$, $R_2$ and X are defined in the specification.

18 Claims, 3 Drawing Sheets

U.S. PATENT DOCUMENTS

| | | | |
|---|---|---|---|
| 6,017,849 | A | 1/2000 | Daly et al. |
| 6,426,319 | B1 | 7/2002 | Kostansek |
| 6,444,619 | B1 | 9/2002 | Kostansek |
| 6,548,448 | B2 | 4/2003 | Kostansek |
| 6,762,153 | B2 | 7/2004 | Kostansek et al. |
| 6,953,540 | B2 * | 10/2005 | Chong et al. .................. 264/4.3 |
| 2005/0065033 | A1 * | 3/2005 | Jacobson et al. .............. 504/343 |

OTHER PUBLICATIONS

Mizojiri et al., Generation of a Silylethylene-Titanium Alkoxide Complex; 2000; J. Org. Chem., 65:6217-6222.*

Martinez-Romero et al., "1-Methylcyclopropene Increases Storability and Shelf Life in Climacteric and Nonclimacteric Plums," Journal of Agricultural and Food Chemistry, vol. 51, pp. 4680-4686, 2003.

Arquiza et al., "1-Methylcyclopropene Interactions With Diphenylamine on Diphenylamine Degradation, α-Farnesene and Conjugated Trienol Concentrations, and Polyphenol Oxidase and Peroxidase Activities in Apple Fruit," Journal of Agricultural and Food Chemistry, vol. 53, pp. 7565-7570, 2005.

Argenta et al. "Influence of 1-Methylcyclopropene on Ripening, Storage Life, and Volatile Production by D'Anjou CV. Pear Fruit," Journal of Agricultural and Food Chemistry, vol. 51, pp. 3858-3864, 2003.

Botondi et al., "Influence of Ethylene Inhibition by 1-Methylcyclopropene on Apricot Quality, Volatile Production, and Glycosidase Activity of Low- and High-Aroma Varieties of Apricots," Journal of Agricultural and Food Chemistry, vol. 51, pp. 1189-1200, 2003.

Fan et al., "Impact of 1-Methylcyclopropene and Methyl Jasmonate on Apple Volatile Production," Journal of Agricultural and Food Chemistry, vol. 47, pp. 2847-2853, 1999.

Mizojiri et al., "Generation of a Silylethylene-Titanium Alkoxide Complex. A Versatile Reagent for Silylethylation and Silylethylidenation of Unsaturated Compounds," Journal of Organization Chemistry, vol. 65, 6217-6222, 2000.

* cited by examiner

METHOD OF PREPARING 1-METHYLCYCLOPROPENE AND APPLYING THE SAME TO PLANTS

BACKGROUND OF THE INVENTION

1. Field of the Invention

The present invention relates to a method for preparing 1-methylcyclopropene and applying the same to plants. More specifically, the present invention relates to a method for directly preparing in situ 1-methylcyclopropene, which inhibits the action of ethylene of accelerating the ripening process of plants, wherein the preparation is carried out by reacting a predetermined 1-methylcyclopropene precursor with a base or a fluoride anion material, and applying the 1-methylcyclopropene to plants.

2. Description of the Related Art

Ethylene ($C_2H_4$) accelerates the ripening process of plants, while cyclopropene compounds inhibit the action of ethylene in plants [U.S. Pat. No. 5,518,988].

Of these cyclopropene compounds, 1-methylcyclopropene (simply referred to as "1-MCP") of the following Formula 1 exhibits potent efficacy.

(1)

Because 1-MCP is gas even at ambient temperature (b.p: ~10° C./760 mmHg), it can be easily applied throughout a storage space of agricultural products without any additional spraying device. For this reason, 1-MCP is widely used to store fruits, flowers and vegetables such as apples, pears, persimmons, plums, kiwis, lilies and carnations for a longer time [J. Agric. Food Chem. 53 (2005), 7565~7570; J. Agric. Food Chem. 51(2003), 4680~4686; J. Agric. Food Chem. 51(2003), 3858~3864; J. Agric. Food Chem. 51(2003), 1189~1200; J. Agric. Food Chem. 47 (1999), 2847~2853].

However, because most of cyclopropene compounds including 1-MCP are chemically unstable, they can be stored safely only at ultra-low temperature. For this reason, specific methods to store 1-MCP for a long time were developed and utilized in the storage of agricultural products [U.S. Pat. Nos. 6,017,849, 6,426,319, 6,444,619, 6,548,448, 6,762,153 and 6,953,540].

Meanwhile, instead of a method to store chemically unstable 1-MCP, a new attempt to use 1-MCP without storing process at the same time as the preparation was made. For example, the inventor of the present invention suggested a method or device which is capable of applying to plants at the same time as the in situ preparation of cyclopropene compounds including 1-MCP (Korean Patent Application No. 2006-0048121).

This patent discloses preparation of 1-MCP using a variety of chemical reactions and in particular, preparation of cyclopropene compounds by mixing β-halocyclopropylsilane compounds or their chemical equivalents thereof with fluoride ions ($F^-$). Wherein, β-halocyclopropylsilane compounds or their chemical equivalents containing trimethylsilane substitutes (trimethylsilyl, TMS) are the most convenient and economical to prepare.

However, it was newly confirmed that the preparation of cyclopropene compounds from TMS-containing compounds yields fluorotrimethylsilane ($Me_3SiF$) as a by-product which is very harmful to plants as well as human beings. As the result, fluorotrimethylsilane is disadvantageously discharged together with 1-MCP, because its boiling point (16° C./760 mmHg) is very similar to 1-MCP's (~10° C./760 mmHg). Accordingly, an additional process or device to remove fluorotrimethylsilane is indispensable thereof.

SUMMARY OF THE INVENTION

Therefore, the present invention has been made to solve the above problems, and other technical problems that have yet to be resolved.

As a result of extensive and intensive studies and experiments associated with Korean Patent Application No. 2006-0048121, the inventor of the present invention has discovered that 1-MCP can be prepared in situ without causing highly volatile harmful by-products, fluorosilane (e.g., (fluorotrimethylsilane) and can thus be applied to plants without any filtering device. The invention has been completed based on this finding. In accordance with an aspect of the invention, the above and other objects can be accomplished by the provision of a method for directly preparing in situ 1-methylcyclopropene which inhibits the action of ethylene of accelerating the ripening process of plants, which comprises reacting a predetermined 1-methylcyclopropene precursor represented by the following Formula 2 or 3 with a base or fluoride anion material, and applying the 1-methylcyclopropene to plants.

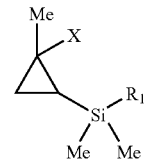

(2)

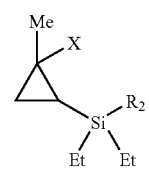

(3)

wherein

Me is methyl;

Et is ethyl;

$R_1$ is substituted or unsubstituted $C_2$-$C_{10}$ alkyl or $C_6$-$C_{10}$ aryl;

$R_2$ is substituted or unsubstituted $C_1$-$C_{10}$ alkyl or $C_6$-$C_{10}$ aryl; and X is $OSO_2T$, in which T is substituted or unsubstituted $C_1$-$C_{10}$ alkyl or $C_6$-$C_{10}$ aryl.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
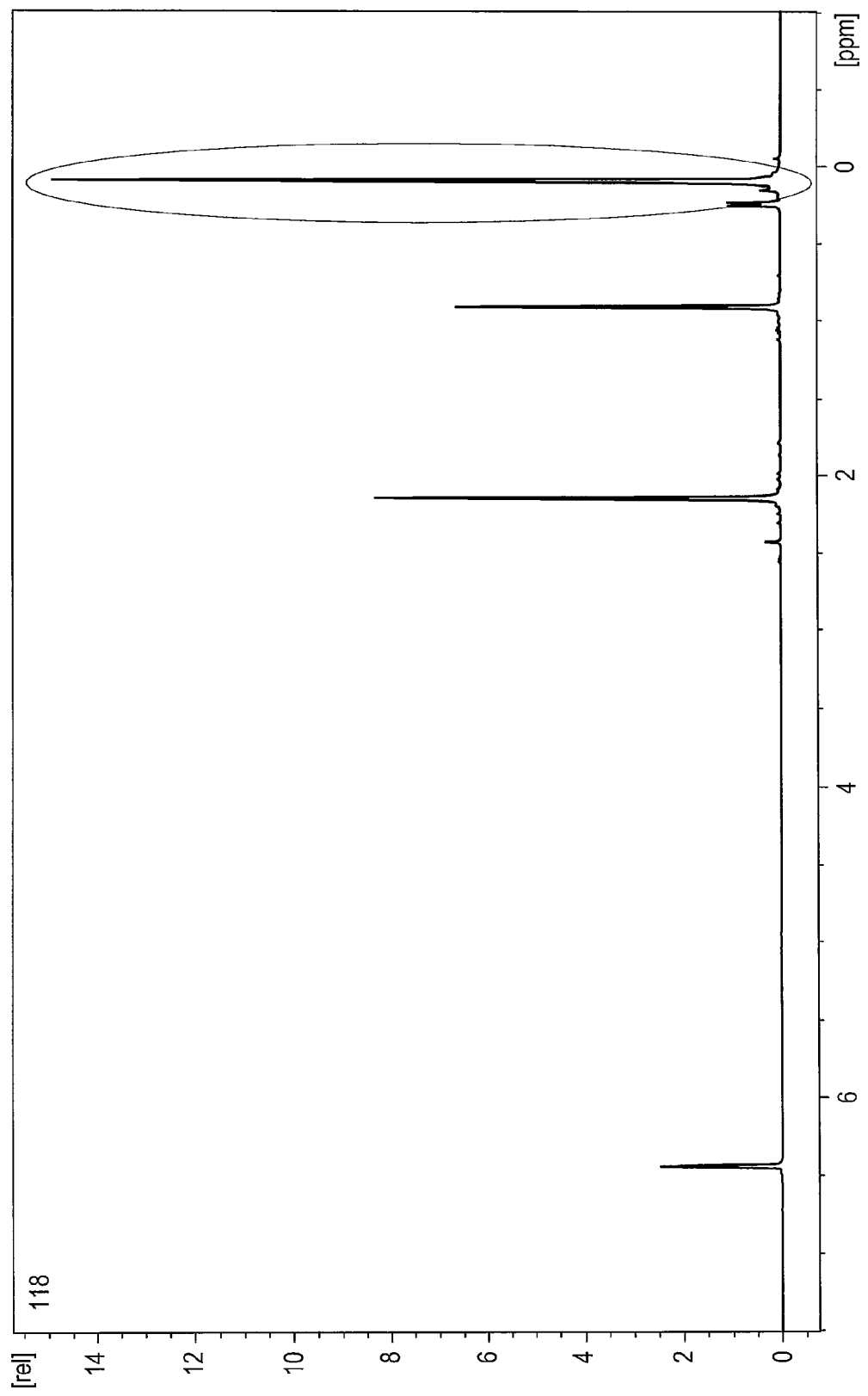
FIG. 1 is a $^1$H-NMR spectrum of liquid trapped using a 1-MCP precursor obtained in comparative Example 1, in Experimental Example 1; and (1)

Hereinafter, the present invention will be described in more detail.

As used herein, the term "substituted alkyl" refers to an alkyl substituted by hydroxy, halogen, alkoxy, cycloalkyl, aryl, amine, nitro, or the like. In addition, the term "substituted aryl" refers to an aryl substituted by lower alkyl, alkoxy, or the like.

According to the present invention, as can be seen from Experimental Examples as described below, only 1-MCP can be prepared in situ without producing any volatile harmful byproduct (i.e., fluorosilane) and thus be applied to plants directly without any additional filtering device or process.

As used herein, the term "without producing any harmful byproduct, fluorosilane" means that when 1-MCP is applied to plants, fluorosilane together therewith is not applied thereto. That is, fluorosilane generated in the process of preparing 1-MCP by the reaction of the compounds of Formulae 2 and 3 with a base or a fluoride anion material remains in the container and is thus not released in or around plants during application of 1-MCP to the plants, due to the difference in boiling point between the compound and 1-MCP, and modification caused by the reaction with moisture.

A variety of methods for applying 1-MCP to plants may be used in the present invention. For example, a simple treatment of gaseous 1-MCP may be very useful for application but the present invention is not limited thereto. In this regard, an apparatus for preparing 1-MCP in situ from 1-MCP precursors and a method associated therewith are disclosed in Korean Patent Application No. 2006-0048121, which is incorporated by reference herein in its entirety.

In an preferred embodiment, $R_1$ is selected from ethyl, propyl, butyl, isobutyl, pentyl, hexyl, octyl, phenyl, toluoyl, methoxyphenyl, 3-methoxypropyl and the like, and is more preferably $C_2$-$C_8$ alkyl or $C_6$-$C_8$ aryl;

$R_2$ is selected from methyl, ethyl, propyl, butyl, isobutyl, pentyl, hexyl and the like, and is more preferably methyl; and X is selected from methanesulfonyloxy, ethanesulfonyloxy, propanesulfonyloxy, butanesulfonyloxy, isopropanesulfonyloxy, benzenesulfonyloxy, toluenesulfonyloxy and the like.

The compound of Formula 2 may be synthesized in accordance with a series of processes depicted in the following Reaction Scheme, based on the method reported by Fumie Sato, et al. (J. Org. Chem. 65 (2000), 6217~6222).

[Reaction Scheme 1]

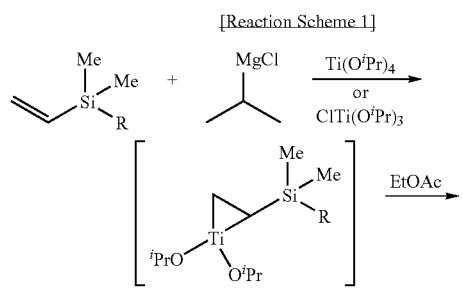

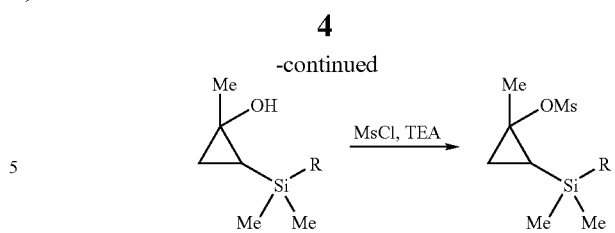

In Reaction Scheme 1, R is as defined above for $R_1$.

A more detailed explanation of the synthesis is as follows. Alkyldimethylvinylsilane reacts with an isopropyl Grignard reagent and titanium (IV) isopropoxide or chlorotitanium (IV) triisopropoxide to prepare a titanium (II) solution and the solution reacts with ethyl acetate to prepare a mixture of trans and cis isomers of 1-hydroxy-1-methylcyclopropane in a ratio of 2:1 to 4:1. The mixture reacts with methanesulfonyl chloride to prepare a compound of Formula 2. A detailed explanation for the synthetic method of this compound will be given with reference to specific examples which follow.

The compound of Formula 3 may be synthesized in accordance with the following Reaction Scheme 2, which is substantially the same as in the compound of Formula 2. When compared with the compound of Formula 2, the compounds of Formula 3 except for compounds wherein $R_2$ is methyl have several disadvantages. More specifically, the compounds of Formula 3 except for compound wherein $R_2$ is methyl have a yield due to cyclization using Ti (IV) which is 10 to 40% lower than that of the compound of Formula 2, cis isomers thereof are nearly unreactive with methanesulfonylchloride and chemical stability thereof is relatively low. The low chemical stability will be due to an increased intra-molecular steric hindrance derived from alkydiethylsilyl group in the compound of Formula 3. That is, except for case wherein $R_2$ is methyl, even though still useful as a 1-MCP precursor, the compound of Formula 3 is not attractive from the practical point of view, as compared to the compound of Formula 2.

[Reaction Scheme 2]

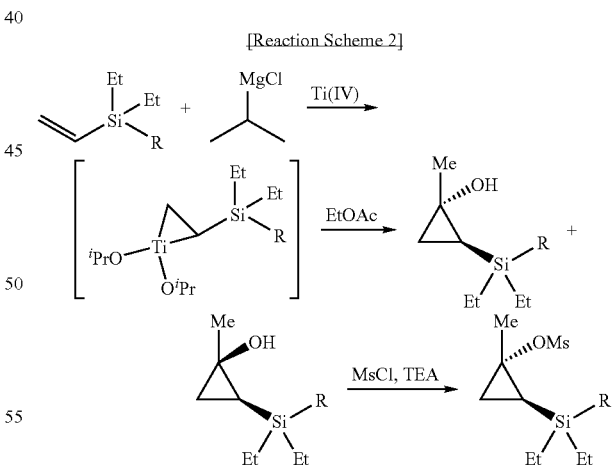

In Reaction Scheme 2, R is as defined above for $R_2$.

Suitable bases used for the method include weak or strong bases well-known in the art, and examples of suitable fluoride ion materials include fluoride salts in the form of alkyl or aryl ammonium salts such as $Bu_4NF$, $Pr_3NF$, $Me_4NF$, $Et_4NF$, $Pentyl_4NF$, $Hexyl_4NF$, $BnBu_3NF$, $BnPr_3NF$, $BnMe_3NF$ and $BnEt_3NF$, and inorganic fluoride salts such as NaF, LiF or KF.

In addition, 1-MCP can be prepared in a simple process to mix the fluoride anion material with the compound of Formula 2 or 3. Preferably, the fluoride anion material is tetraalkylammonium fluoride represented by Formula 4 below:

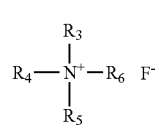
(4)

wherein $R_3$, $R_4$, $R_5$ and $R_6$ are each independently $C_1$-$C_{20}$ alkyl or $C_6$-$C_{10}$ aryl.

As mentioned above, fluorosilane obtained in the process of preparing 1-MCP in accordance with the present invention remains in the container and is not released to or in or around plants.

For example, the compound of Formula 2 yields fluorosilane represented by the following Formula 5, as a byproduct, which reacts with neighboring water ($H_2O$) to produce siloxane represented by Formula 6. This process is depicted in the following Reaction Scheme 3.

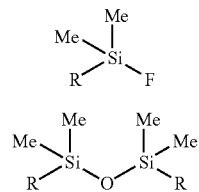
(5)
(6)

[Reaction Scheme 3]

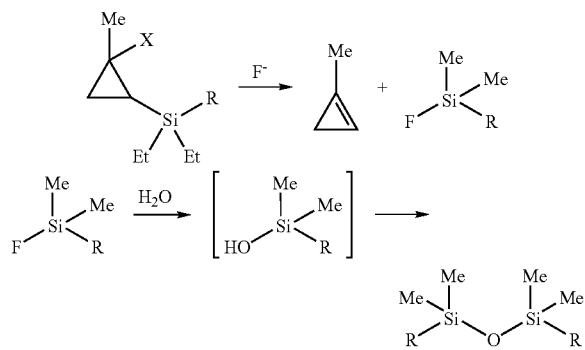

In Formulae 5 and 6, and Reaction Scheme 3, R is as defined above for $R_1$.

As such, when 1-MCP is prepared from the compound of Formula 2, rather than fluorotrimethylsilane, alkyldimethylfluorosilane of Formula 4 is generated as a by-product. Due to considerably high boiling point resulted from its increased molecular weight, as compared to fluorotrimethylsilane, alkyldimethylfluorosilane is not released to the air together with 1-MCP. In addition, alkyldimethylfluorosilane is modified into a non-volatile substance via reaction with moisture. As a result, alkyldimethylfluorosilane is not applied to plants during application of 1-MCP thereto. Accordingly, 1-MCP can be more safely and conveniently prepared by using the compound of Formula 2 as a 1-MCP precursor. Similar results can be obtained in the case of the compound of Formula 3.

Also, the present invention provides a compound represented by Formula 2 or 3, useful as a 1-MCP precursor which reacts with a base or a fluoride anion material to synthesize 1-MCP.

The afore-mentioned compounds are inherently novel, thus preventing byproducts, namely, fluorosilane, from being applied to plants in the process of preparing 1-MCP and applying the same thereto, as mentioned above, and requiring no process or device to separate the byproducts from 1-MCP.

EXAMPLES

Now, the present invention will be described in more detail with reference to the following Examples. These examples are provided only for illustrating the present invention and should not be construed as limiting the scope and sprit of the present invention.

Comparative Example 1

Synthesis of 1-methyl-1-(methanesulfonyloxy)-2-(trimethylsilyl)cyclopropane (1) Synthesis of 1-methyl-1-hydroxy-2-(trimethylsilyl)cyclopropane 20.2 g (0.83 mole) of magnesium and 300 ml of ethyl ether were placed in a 1,000 ml three-neck round bottom flask, and 65 g (0.82 mole) of 2-chloropropane was slowly added thereto, to prepare a Grignard solution. Meanwhile, 114 g (0.40 mole) of titanium (IV) isopropoxide and 40.0 g (0.40 mole) of vinyltrimethylsilane were placed in another 1,000 ml three-neck round bottom flask cooled to −78° C., and the above-prepared Grignard solution was gradually added thereto for 30 minutes. The reaction solution thus obtained was warmed to −50° C. and then vigorously stirred for 2 hours. 36 g (0.4 mole) of ethyl acetate was gradually added over 30 min, while the reaction solution was maintained at −50° C. The reaction solution was warmed to −20° C., vigorously stirred for 1 hour, warmed to 0° C., and then vigorously stirred for another 1 hour. Finally, the reaction solution was warmed to room temperature and 70 mL of saturated brine was added to the solution. The resulting solution was filtered through Celite which was then thoroughly washed once more with 20 mL of ether. The filtrate thus obtained was dried over anhydrous magnesium sulfate ($MgSO_4$) and was concentrated by the evaporation of solvent under reduced vacuum at a low temperature of 30° C. or less. The resulting concentrate was distilled (35-50° C./0.1 mmHg) under vacuum to obtain 27.8 g (0.21 mole, yield: 52%) of 1-methyl-1-hydroxy-2-(trimethylsilyl)cyclopropane as a mixture of two isomers, i.e., trans and cis isomers. Although these isomers may be used directly without any further purification, the trans and cis isomers were separated by silica gel chromatography for structural analysis. The analysis results ascertained that the trans and cis isomers are present in a ratio of about 3:1.

Results of $^1$H-NMR and $^{13}$C-NMR for the trans isomer of the mixture are given below.

$^1$H-NMR (CDCl$_3$, δ): 2.06 (1H, b, —OH), 1.452 (1H, s), 0.976 (1H, dd), 0.382 (1H, dd), 0.044 (1H, dd), 0.018 (9H, s)

$^{13}$C-NMR (CDCl$_3$, δ): 56.191, 23.476, 18.204, 14.097, −0.968.

Results of $^1$H-NMR and $^{13}$C-NMR for the cis isomer of the mixture are given below.

$^1$H-NMR (CDCl$_3$, δ): 1.64 (1H, b, —OH), 1.487 (1H, s), 0.74~0.65 (2H, m), 0.048 (9H, s), −0.296 (1H, dd).

$^{13}$C-NMR (CDCl$_3$, δ): 57.229, 27.114, 18.126, 14.400, −0.678.

(2) Synthesis of 1-methyl-1-(methanesulfonyloxy)-2-(trimethylsilyl)cyclopropane 16 g (0.11 mole) of a trans isomer, a cis isomer or a trans/cis isomer mixture of 1-methyl-1-hydroxy-2-(trimethylsilyl)cyclopropane, prepared in Section (1) was dissolved in 150 ml of dichloromethane and 25 ml of triethylamine was added thereto. The reaction solution was cooled to 0° C., 16 g (0.14 mole) of methanesulfonylchloride was gradually added thereto and the mixture was vigorously stirred for 1 hour. 50 mL of a saturated aqueous NaHCO$_3$ solution was added to the reaction mixture to complete the reaction. An organic layer was separated from the reaction solution, dried over anhydrous magnesium sulfate (MgSO$_4$), and concentrated by distillation of the solvent. Although the concentrate may be used directly without any further purification, it was finely purified by vacuum distillation (55-60° C./0.1 mmHg). As a result, 21.4 g (0.0096 mole, yield: 87%) of 1-methyl-1-(methanesulfonyloxy)-2-(trimethylsilyl)cyclopropane was obtained as a trans isomer, a cis isomer and a mixture thereof.

Results of $^1$H-NMR and $^{13}$C-NMR for the trans isomer of the mixture are given below.

$^1$H-NMR (CDCl$_3$, δ): 2.964 (3H, s), 1.700 (3H, s), 1.394 (1H, dd), 0.577 (1H, dd), 0.539 (1H, dd), 0.051 (9H, s).

$^{13}$C-NMR (CDCl$_3$, δ): 67.280, 39.996, 21.434, 15.951, 12.636, −1.332.

Results of $^1$H-NMR and $^{13}$C-NMR for the cis isomer of the mixture are given below.

$^1$H-NMR (CDCl$_3$, δ): 2.973 (3H, s), 1.754 (3H, s), 1.379 (1H, dd), 1.028 (1H, dd), 0.076 (9H, s), −0.180 (1H, dd).

$^{13}$C-NMR (CDCl$_3$, δ): 68.733, 39.936, 24.373, 16.950, 11249, −1.193.

Example 1

Synthesis of 1-methyl-1-(methanesulfonyloxy)-2-(dimethylethylsilyl)cyclopropane (1) Synthesis of 1-methyl-1-hydroxy-2-(dimethylethylsilyl)cyclopropane 47.3 g (0.17 mole) of titanium (IV) isopropoxide and 19 g (0.17 mole) of dimethylethylvinylsilane were placed in a 500 ml three-neck round bottom flask cooled to −78° C., and 0.34 mole of an isopropylmagnesium chloride Grignard solution was gradually added thereto for 2 hours. The reaction solution thus obtained was warmed to −50° C. and then vigorously stirred for 2 hours. 14.7 g (0.17 mole) of ethyl acetate was gradually added over 30 min, while the reaction solution was maintained at −50° C. The reaction solution was warmed to −20° C., vigorously stirred for 1 hour, warmed to 0° C., and then vigorously stirred for another 1 hour. Finally, the reaction solution was warmed to room temperature and 60 mL of saturated brine was added to the solution. The resulting solution was filtered through Celite which was then thoroughly washed once more with 100 mL of ether. The filtrate thus obtained was dried over anhydrous magnesium sulfate (MgSO$_4$), and was concentrated by the evaporation of solvent under reduced vacuum at a low temperature of 30° C. or less. The resulting concentrate was distilled under vacuum (40-65° C./0.1 mmHg) to obtain 14.6 g (0.092 mole, yield: 54%) of 1-methyl-1-hydroxy-2-(trimethylsilyl)cyclopropane as a mixture of trans and cis isomers in a ratio of about 3:1. Although they may be used directly without any further purification, the trans and cis isomers were separated by silica gel chromatography and their structures were confirmed.

Results of $^1$H-NMR and $^{13}$C-NMR for the trans isomer of the mixture are given below.

$^1$H-NMR (CDCl$_3$, δ): 1.990 (1H, b, —OH), 1.452 (3H, s), 0.976 (1H, dd), 0.956 (3H, t), 0.516 (2H, q), 0.386 (1H, dd), 0.042 (1H, dd), −0.016 (3H, s), −0.048 (3H, s).

$^{13}$C-NMR (CDCl$_3$, δ): 56.178, 23.658, 18.231, 12.938, 7.709, 7.376, −3.262, −3.506.

Results of $^1$H-NMR and $^{13}$C-NMR for the cis isomer of the mixture are given below.

$^1$H-NMR (CDCl$_3$, δ): 1.545 (1H, b, —OH), 1.486 (3H, s), 0.964 (3H, t), 0.72~0.66 (2H, m), 0.57~0.51 (2H, m), 0.012 (3H, s), 0.004 (3H, s), −0.303 (1H, dd).

$^{13}$C-NMR (CDCl$_3$, δ): 56.988, 27.086, 18.018, 13.105, 7.863, 7.468, −3.047, −3.107.

(2) Synthesis of 1-methyl-1-(methanesulfonyloxy)-2-(dimethylethylsilyl)cyclopropane 1.6 g (0.010 mole) of a trans isomer, a cis isomer or a trans/cis isomer mixture of 1-methyl-1-hydroxy-2-(trimethylsilyl)cyclopropane, prepared in Section (1), was dissolved in 15 ml of dichloromethane and 23 g of triethylamine was added thereto. The reaction solution was cooled to 0° C., 1.3 g (0.011 mole) of methanesulfonyl chloride was gradually added thereto and the mixture was vigorously stirred for 1 hour. 5 mL of a saturated aqueous NaHCO$_3$ solution was added to the reaction mixture to complete the reaction. An organic layer was separated from the reaction solution, dried over anhydrous magnesium sulfate (MgSO$_4$), and concentrated by distillation of the solvent at a low temperature of 30° C. or less. Although the concentrate may be used directly without any further purification, it was purified over silica gel again to obtain 1.74 g (7.3 mmole, yield: 74%) of 1-methyl-1-(methanesulfonyloxy)-2-(trimethylethylsilyl)cyclopropane.

Results of $^1$H-NMR and $^{13}$C-NMR for the trans isomer of the mixture are given below.

$^1$H-NMR (CDCl$_3$, δ): 2.942 (3H, s), 1.670 (3H, s), 1.370 (1H, dd), 0.947 (3H, t), 0.59~0.49 (4H, m), 0.015 (3H, s), −0.023 (3H, s).

$^{13}$C-NMR (CDCl$_3$, δ): 67.187, 39.948, 21.553, 15.889, 11.399, 7.283, 7.101, −3.662, −3.864.

Results of $^1$H-NMR and $^{13}$C-NMR for the cis isomer of the mixture are given below.

$^1$H-NMR (CDCl$_3$, δ): 2.942 (3H, s), 1.670 (3H, s), 1.370 (1H, dd), 0.947 (3H, t), 0.59~0.49 (4H, m), 0.015 (3H, s), −0.023 (3H, s).

$^{13}$C-NMR (CDCl$_3$, δ): 68.543, 39.911, 24.354, 16.864, 11.942, 7.425, 7.319, −3.563, −3.602.

Example 2

Synthesis of 1-methyl-1-(methanesulfonyloxy)-2-(dimethylpropylsilyl)cyclopropane (1) Synthesis of 1-methyl-1-hydroxy-2-(dimethylpropylsilyl)cyclopropane 1-methyl-1-hydroxy-2-(dimethylpropylsilyl)cyclopropane was obtained as a mixture of trans and cis isomers (yield: 52%) using dimethylpropylvinylsilane in the same manner as in Example 1 (1).

Results of $^1$H-NMR and $^{13}$C-NMR for the trans isomer of the mixture are given below.

¹H-NMR (CDCl₃, δ): 2.078 (1H, b, —OH), 1.446 (3H, s), 1.374 (2H, m), 0.971 (1H, m), 0.962 (3H, t), 0.529 (2H, m), 0.376 (1H, dd), 0.044 (1H, dd), −0.019 (3H, s), −0.047 (3H, s).
¹³C-NMR (CDCl₃, δ): 56.315, 23.670, 18.758, 18.346, 18.282, 17.395, 13.366, −2.675, −2.934.
Results of ¹H-NMR and ¹³C-NMR for the cis isomer of the mixture are given below.
¹H-NMR (CDCl₃, δ): 1.667 (1H, b, —OH), 1.474 (3H, s), 1.371 (2H, m), 0.962 (3H, t), 0.72~0.65 (2H, m), 0.58~0.54 (2H, m), 0.007 (3H, s), 0.000 (3H, s), −0.316 (1H, dd).
¹³C-NMR (CDCl₃, δ): 57.113, 27.122, 18.952, 18.367, 18.051, 17.499, 13.502, −2.473, −2.526.

(2) Synthesis of 1-methyl-1-(methanesulfonyloxy)-2-(dimethylpropylsilyl)cyclopropane 1-methyl-1-(methanesulfonyloxy)-2-(dimethylpropylsilyl)cyclopropane was obtained as a mixture of trans and cis isomers (yield: 88%) in the same manner as in Example 1 (2).
Results of ¹H-NMR and ¹³C-NMR for the trans isomer of the mixture are given below.
¹H-NMR (CDCl₃, δ): 2.932 (3H, s), 1.660 (3H, s), 1.355 (3H, m), 0.937 (3H, t), 0.57~0.48 (4H, m), 0.012 (3H, s), −0.036 (3H, s).
¹³C-NMR (CDCl₃, δ): 67.197, 39.917, 21.510, 18.182, 18.161, 17.086, 15.876, 11.683, −3.102, −3.352.
Results of ¹H-NMR and ¹³C-NMR for the cis isomer of the mixture are given below.
¹H-NMR (CDCl₃, δ): 2.943 (3H, s), 1.719 (3H, s), 1.345 (3H, m), 0.998 (1H, dd), 0.941 (3H, t), 0.58~0.54 (2H, m), 0.011 (3H, s), 0.000 (3H, s), −0.223 (1H, dd).
¹³C-NMR (CDCl₃, δ): 68.469, 39.824, 24.256, 18.344, 18.187, 17.220, 16.777, 12.202, −3.101, −3.123.

Example 3

Synthesis of 1-methyl-1-(methanesulfonyloxy)-2-dimethylbutylsilyl)cyclopropane (1) Synthesis of 1-methyl-1-hydroxy-2-(dimethylbutylsilyl)cyclopropane 1-methyl-1-hydroxy-2-(dimethylbutylsilyl)cyclopropane was obtained as a trans isomer, a cis isomer or a trans/cis isomer mixture (yield: 54%) using dimethylbutylvinylsilane in the same manner as in Example 1 (1).
Results of ¹H-NMR ¹³C-NMR for the trans isomer of the mixture are given below.
¹H-NMR (CDCl₃, δ): 2.896 (1H, s, —OH), 1.413 (3H, s), 1.303 (4H, m), 0.945 (1H, dd), 0.863 (3H, t), 0.506 (2H, m), 0.337 (1H, dd), 0.004 (1H, dd), −0.036 (3H, s), −0.069 (3H, s).
¹³C-NMR (CDCl₃, δ): 56.044, 26.545, 26.078, 23.597, 18.107, 15.773, 13.754, 13.070, −2.737, −3.026.
Results of ¹H-NMR and ¹³C-NMR for the cis isomer of the mixture are given below.
¹H-NMR (CDCl₃, δ): 1.63 (1H, b, —OH), 1.459 (3H, s), 1.38-1.25 (4H, m), 0.865 (3H, t), 0.72~0.65 (2H, m), 0.59~0.54 (2H, m), 0.011 (3H, s), 0.003 (3H, s), −0.327 (1H, dd).
¹³C-NMR (CDCl₃, δ): 57.102, 27.131, 26.269, 26.102, 18.073, 15.973, 13.854, 13.800, 13.479, −2.504, −2.574.

(2) Another Synthetic Example of 1-methyl-1-hydroxy-2-(dimethylbutylsilyl)cyclopropane 41.6 g (0.16 mole) of titanium (IV) chloride triisopropoxide, 22.8 g (0.16 mole) of dimethylvinylsilane and 15.0 g (0.17 mol) of ethyl acetate were placed in a 1,000 ml three-neck round bottom flask cooled to −78° C., and 0.33 mol of an isopropylmagnesium chloride Grignard solution was gradually added thereto for 2 hours, with vigorous stirring. The reaction solution thus obtained was warmed to −20° C. and then vigorously stirred for one hour. The reaction solution was warmed to 0° C. and then vigorously stirred for another 1 hour. The resulting solution was warmed to room temperature and 50 mL of saturated brine was added to the solution. The resulting solution was filtered through Celite which was then thoroughly washed once more with 100 mL of ether. The filtrate thus obtained was dried over anhydrous magnesium sulfate (MgSO₄) and concentrated by the evaporation of solvent at a low temperature of 30° C. or less. The resulting concentrate was distilled (75-90° C./0.1 mmHg) under high vacuum to obtain 15.5 g (0.083 mole) of 1-methyl-1-hydroxy-2-(trimethylsilyl)cyclopropane as a mixture of trans and cis isomers in a ratio of about 3:1. The major isomer of the mixture was a trans isomer. The above-mentioned method was slightly different in terms of yield (52%) from the method using titanium (IV) isopropoxide, and was substantially equivalent thereto in terms of reaction routes.

(3) Synthesis of 1-methyl-1-(methanesulfonyloxy)-2-(dimethylbutylsilyl)cyclopropane 1-methyl-1-(methanesulfonyloxy)-2-(dimethylbutylsilyl) cyclopropane was obtained as a trans isomer, a cis isomer or a trans/cis isomer mixture (yield: 84%) in the same manner as in Example 1 (2).
Results of ¹H-NMR and ¹³C-NMR for the trans isomer of the mixture are given below.
¹H-NMR (CDCl₃, δ): 2.935 (3H, s), 1.664 (3H, s), 1.365 (1H, dd), 1.305 (4H, m), 0.856 (3H, t), 0.57~0.49 (4H, m), 0.017 (3H, s), −0.034 (3H, s).
¹³C-NMR (CDCl₃, δ): 67.207, 39.923, 26.396, 25.768, 21.527, 15.899, 15.255, 13.665, 11.661, −3.125, −3.401.
Results of ¹H-NMR and ¹³C-NMR for the cis isomer of the mixture are given below.
¹H-NMR (CDCl₃, δ): 2.976 (3H, s), 1.758 (3H, s), 1.384 (1H, dd), 1.317 (4H, m), 1.037 (1H, dd), 0.892 (3H, t), 0.61~0.56 (2H, m), 0.045 (3H, s), 0.033 (3H, s), −0.194 (1H, dd).
¹³C-NMR (CDCl₃, δ): 68.645, 39.938, 26.509, 26.050, 24.413, 16.925, 15.499, 13.821, 12.310, −3.049.

Example 4

Synthesis of 1-methyl-1-(methanesulfonyloxy)-2-(dimethylhexylsilyl)cyclopropane (1) Synthesis of 1-methyl-1-hydroxy-2-(dimethylhexylsilyl)cyclopropane 1-methyl-1-hydroxy-2-(dimethylhexylsilyl)cyclopropane was obtained as a mixture of trans and cis isomers (yield: 43%) using dimethylhexylvinylsilane in the same manner as in Example 1 (1).
Results of ¹H-NMR and ¹³C-NMR for the trans isomer of the mixture are given below.
¹H-NMR (CDCl₃, δ): 1.914 (1H, s, —OH), 1.454 (3H, s), 1.27 (8H, m), 0.980 (1H, dd), 0.882 (3H, t), 0.525 (2H, m), 0.386 (1H, dd), 0.041 (1H, dd), −0.013 (3H, s), −0.044 (3H, s).
¹³C-NMR (CDCl₃, δ): 56.362, 33.321, 31.597, 23.849, 23696, 22.616, 18.337, 16.089, 14.139, 13.404, −2.700, −2.976.

(2) Synthesis of 1-methyl-1-(methanesulfonyloxy)-2-(dimethylhexylsilyl)cyclopropane 1-methyl-1-(methanesulfonyloxy)-2-(dimethylhexylsilyl)cyclopropane was obtained as a trans isomer (yield: 74%) in the same manner as in Example 1 (2).

Results of $^1$H-NMR and $^{13}$C-NMR for the trans isomer of the mixture are given below.

$^1$H-NMR (CDCl$_3$, δ): 2.967 (3H, s), 1.696 (3H, s), 1.403 (1H, dd), 1.33~11.27 (8H, m), 0.880 (3H, t), 0.59~0.51 (4H, m), 0.046 (3H, s), −0.006 (3H, s).

$^{13}$C-NMR (CDCl$_3$, δ): 67.425, 40.040, 33.240, 31.543, 23.629, 22.586, 21.645, 16.028, 15.667, 14.121, 11.788, −3.007, −3.283.

Example 5

Synthesis of 1-methyl-1-(methanesulfonyloxy)-2-(dimethyl(3-methoxypropyl)silyl)cyclopropane (1) Synthesis of 1-methyl-1-hydroxy-2-(dimethyl(3-methoxypropyl)silyl)cyclopropane 1-methyl-1-hydroxy-2-(dimethyl(3-methoxypropyl)silyl)cyclopropane was obtained as a trans isomer, a cis isomer or a trans/cis isomer mixture (yield: 46%) using dimethyl(3-methoxypropyl)vinylsilane in the same manner as in Example 1 (1).

Results of $^1$H-NMR and $^{13}$C-NMR for the trans isomer of the mixture are given below.

$^1$H-NMR (CDCl$_3$, δ): 3.309 (2H, t), 3.292 (3H, s), 2.961 (1H, b, —OH), 1.566 (2H, m), 1.390 (3H, s), 0.936 (1H, dd), 0.492 (2H, m), 0.324 (1H, dd), −0.023 (1H, dd), −0.045 (3H, s), −0.074 (3H, s).

$^{13}$C-NMR (CDCl$_3$, δ): 75.562, 58.314, 55.797, 23.860, 23.583, 18.111, 12.892, 11.973, −2.876, −3.761.

Results of $^1$H-NMR and $^{13}$C-NMR for the cis isomer of the mixture are given below.

$^1$H-NMR (CDCl$_3$, δ): 3.372 (2H, m), 3.331 (3H, s), 2.064 (1H, b), 1.627 (2H, m), 1.467 (3H, s), 0.72~0.63 (2H, m), 0.62~0.499 (2H, m), 0.013 (6H, s), −0.324 (1H, dd).

$^{13}$C-NMR (CDCl$_3$, δ): 75.674, 58.416, 56.922, 27.075, 24.017, 18.053, 13.205, 12.087, −2.487, −2.573.

(2) Synthesis of 1-methyl-1-(methanesulfonyloxy)-2-(dimethyl(3-methoxypropyl)silyl)cyclopropane 1-methyl-1-(methanesulfonyloxy)-2-(dimethyl(3-methoxypropyl)silyl)cyclopropane was obtained as a trans isomer, a cis isomer or a trans/cis isomer mixture (yield: 82%) in the same manner as in Example 1 (2).

Results of $^1$H-NMR and $^{13}$C-NMR for the trans isomer of the mixture are given below.

$^1$H-NMR (CDCl$_3$, δ): 3.266 (2H, t), 3.245 (3H, s), 2.885 (3H, s), 1.612 (3H, s), 1.57~1.49 (2H, m), 1.311 (1H, dd), 0.54~0.44 (4H, m), −0.017 (3H, s), −0.067 (3H, s).

$^{13}$C-NMR (CDCl$_3$, δ): 75.173, 66.845, 58.193, 39.800, 23.559, 21.415, 15.772, 11.481, 11.403, −3.331, −3.593.

Results of $^1$H-NMR and $^{13}$C-NMR for the cis isomer of the mixture are given below.

$^1$H-NMR (CDCl$_3$, δ): 3.336 (2H, t), 3.322 (3H, s), 2.964 (3H, s), 1.737 (3H, s), 1.64~1.55 (2H, m), 1.372 (1H, dd), 1.022 (1H, dd), 0.61-0.56 (2H, m), 0.046 (3H, s), 0.034 (3H, s), −0.200 (1H, dd).

$^{13}$C-NMR (CDCl$_3$, δ): 75.520, 68.464, 58.447, 39.894, 24.299, 23.913, 16.890, 12.033, 11.740, −3.183, −3.195.

Example 6

Synthesis of 1-methyl-1-(methanesulfonyloxy)-2-(dimethylphenylsilyl)cyclopropane (1) Synthesis of 1-methyl-1-hydroxy-2-(dimethylphenylsilyl)cyclopropane 1-methyl-1-hydroxy-2-(dimethylphenylsilyl)cyclopropane was obtained as only pure trans isomers (yield: 38%) using dimethylphenylvinylsilane in the same manner as in Example 1 (1).

Results of $^1$H-NMR and $^{13}$C-NMR for the trans isomer of the mixture are given below.

$^1$H-NMR (CDCl$_3$, δ): 7.60~7.50 (2H, m), 7.42-7.33 (3H, m), 2.239 (1H, b), 1.398 (3H, s), 1.097 (1H, dd), 0.466 (1H, dd), 0.320 (3H, s), 0.302 (3H, s), 0.294 (1H, dd).

$^{13}$C-NMR (CDCl$_3$, δ): 139.016, 133.740, 128.893, 127.725, 56.339, 23.523, 18.498, 13.396, −2.214, −2.276.

(2) Synthesis of 1-methyl-1-(methanesulfonyloxy)-2-(dimethylphenylsilyl)cyclopropane 1-methyl-1-(methanesulfonyloxy)-2-(dimethylphenylsilyl)cyclopropane was obtained as a trans isomer (yield: 76%) in the same manner as in Example 1 (2).

Results of $^1$H-NMR and $^{13}$C-NMR for the trans isomer of the mixture are given below.

$^1$H-NMR (CDCl$_3$, δ): 7.60~7.50 (2H, m), 7.42~7.31 (3H, m), 2.956 (3H, s), 1.611 (3H, s), 1.498 (1H, dd), 0.823 (1H, dd), 0.599 (1H, dd), 0.387 (3H, s), 0.370 (3H, s).

$^{13}$C-NMR (CDCl$_3$, δ): 137.399, 133.760, 129.213, 127.811, 67.074, 39.920, 21.395, 16.236, 11.954, −2.372, −2.896.

Example 7

Synthesis of 1-methyl-1-(methanesulfonyloxy)-2-(diethylmethylsilyl)cyclopropane (1) Synthesis of 1-methyl-1-hydroxy-2-(diethylmethylsilyl)cyclopropane 1-methyl-1-hydroxy-2-(diethylmethylsilyl)cyclopropane was obtained as a mixture of trans and cis isomers (yield: 35%) using diethylmethylvinylsilane in the same manner as in Example 1 (1).

Results of $^1$H-NMR and $^{13}$C-NMR for the trans isomer of the mixture are given below.

$^1$H-NMR (CDCl$_3$, δ): 1.973 (1H, b, —OH), 1.450 (3H, s), 0.987 (1H, dd), 0.963 (3H, t), 0.950 (3H, t), 0.56~0.48 (2H, m), 0.387 (1H, dd), 0.036 (1H, dd), −0.085 (3H, s).

$^{13}$C-NMR (CDCl$_3$, δ): 56.013, 23.772, 18.167, 11.770, 7.472, 7.342, 5.725, 5.695.

Results of $^1$H-NMR and $^{13}$C-NMR for the cis isomer of the mixture are given below.

$^1$H-NMR (CDCl$_3$, δ): 1.528 (1H, b, —OH), 1.490 (3H, s), 0.99~0.90 (6H, m), 0.72~0.67 (2H, m), 0.59~0.52 (4H, m), −0.032 (3H, s), −0.314 (1H, dd).

$^{13}$C-NMR (CDCl$_3$, δ): 56.728, 27.047, 17.954, 11.926, 7.526, 7.423, 5.908, 5.835.

(2) Synthesis of 1-methyl-1-(methanesulfonyloxy)-2-(diethylmethylsilyl)cyclopropane The trans and cis isomers were reacted in the same manner as in Example 1 (2). However, cis isomers were almost completely unreacted (less than 10%) and only trans isomers of 1-methyl-1-(methanesulfonyloxy)-2-(diethylmethylsilyl)cyclopropane were thus obtained.

Results of $^1$H-NMR and $^{13}$C-NMR for the trans isomer of the mixture are given below.

$^1$H-NMR (CDCl$_3$, δ): 2.954 (3H, s), 1.683 (3H, s), 1.401 (1H, dd), 0.969 (3H, t), 0.948 (3H, t), 0.63~0.50 (6H, m), −0.052 (3H, s).

$^{13}$C-NMR (CDCl$_3$, δ): 67.248, 39.975, 21.752, 15.947, 10.387, 7.230, 7.162, 5.401, 5.341.

Example 8

Synthesis of 1-methyl-1-(methanesulfonyloxy)-2-(triethylsilyl)cyclopropane (1) Synthesis of 1-methyl-1-hydroxy-2-(triethylsilyl)cyclopropane 1-methyl-1-hydroxy-2-(triethylsilyl)cyclopropane (yield: 19%) was obtained using triethylvinylsilane in the same manner as in Example 1 (1) and the compound was almost entirely composed of trans isomers.

Results of $^1$H-NMR and $^{13}$C-NMR for the trans isomer of the mixture are given below.

$^1$H-NMR (CDCl$_3$, δ): 1.434 (3H, s), 1.1~0.91 (2H, m), 0.948 (3H, t), 0.503 (2H, q), 0.403 (1H, dd).

$^{13}$C-NMR (CDCl$_3$, δ): 55.830, 23.936, 18.225, 10.916, 7.524, 4.314.

(2) Synthesis of 1-methyl-1-(methanesulfonyloxy)-2-(triethylsilyl)cyclopropane 1-methyl-1-(methanesulfonyloxy)-2-(triethylsilyl)cyclopropane (yield: 92%) was obtained as a trans isomer in the same manner as in Example 1 (2).

Results of $^1$H-NMR and $^{13}$C-NMR for the trans isomer of the mixture are given below.

$^1$H-NMR (CDCl$_3$, δ): 2.937 (3H, s), 1.672 (3H, s), 1.43~1.36 (1H, m), 0.97~0.91 (9H, m), 0.58~0.49 (8H, m).

$^{13}$C-NMR (CDCl$_3$, δ): 67.197, 39.890, 21.844, 15.984, 9.543, 7.186, 3.421.

EXPERIMENTAL EXAMPLES

Comparison of F-Release Level During Preparation of 1-methylcyclopropene

Experimental Example 1

Evaluation of Fluoride Compound Release Level by $^1$H-NMR and Comparison Thereof 5.5 g (c.a. 17 to 20 mmole) of tetrabutylammonium fluoride hydrate was placed in a three-neck round bottom flask and thoroughly dissolved in 15 ml of DMSO. The round bottom flask was purged with nitrogen at a rate of 100 to 300 ml/min, with stirring in a bath at 25° C., while an injection valve was set such that it came in contact with the bottom of the flask, to thereby induce release of bubbles from the flask to the outside. The gas discharged from the round flask was connected to a trap by aid of a plastic tube. The trap was placed in a dry ice/acetone bath (−78° C.) to condense volatile organic materials and trap the same therein. Under these conditions, 2.23 g (10.0 mmole) of 1-methyl-1-(methanesulfonyloxy)-2-(trimethylsilyl)cyclopropane obtained from Comparative Example 1 was added to the flask. The resulting flask was vigorously stirred in a bath at 25° C. for 2 hours. In this process, the liquid collected in the trap was not further purified and a $^1$H-NMR spectrum thereof was obtained using CDCl$_3$ as a solvent. The $^1$H-NMR thus obtained is shown in FIG. 1.

In addition, 1-MCP was prepared from 1-methyl-1-(methanesulfonyloxy)-2-(dimethylbutylsilyl)cyclopropane and 1-methyl-1-(methanesulfonyloxy)-2-(dimethylphenylsilyl) cyclopropane prepared in Example 3 and Example 6, respectively, trapped and dissolved in CDCl$_3$ without further purification, in the same manner as described above, to thereby obtain a $^1$H-NMR spectrum under the same conditions. The $^1$H-NMR spectra thus obtained are shown in FIGS. 2 and 3.

Figure 2:
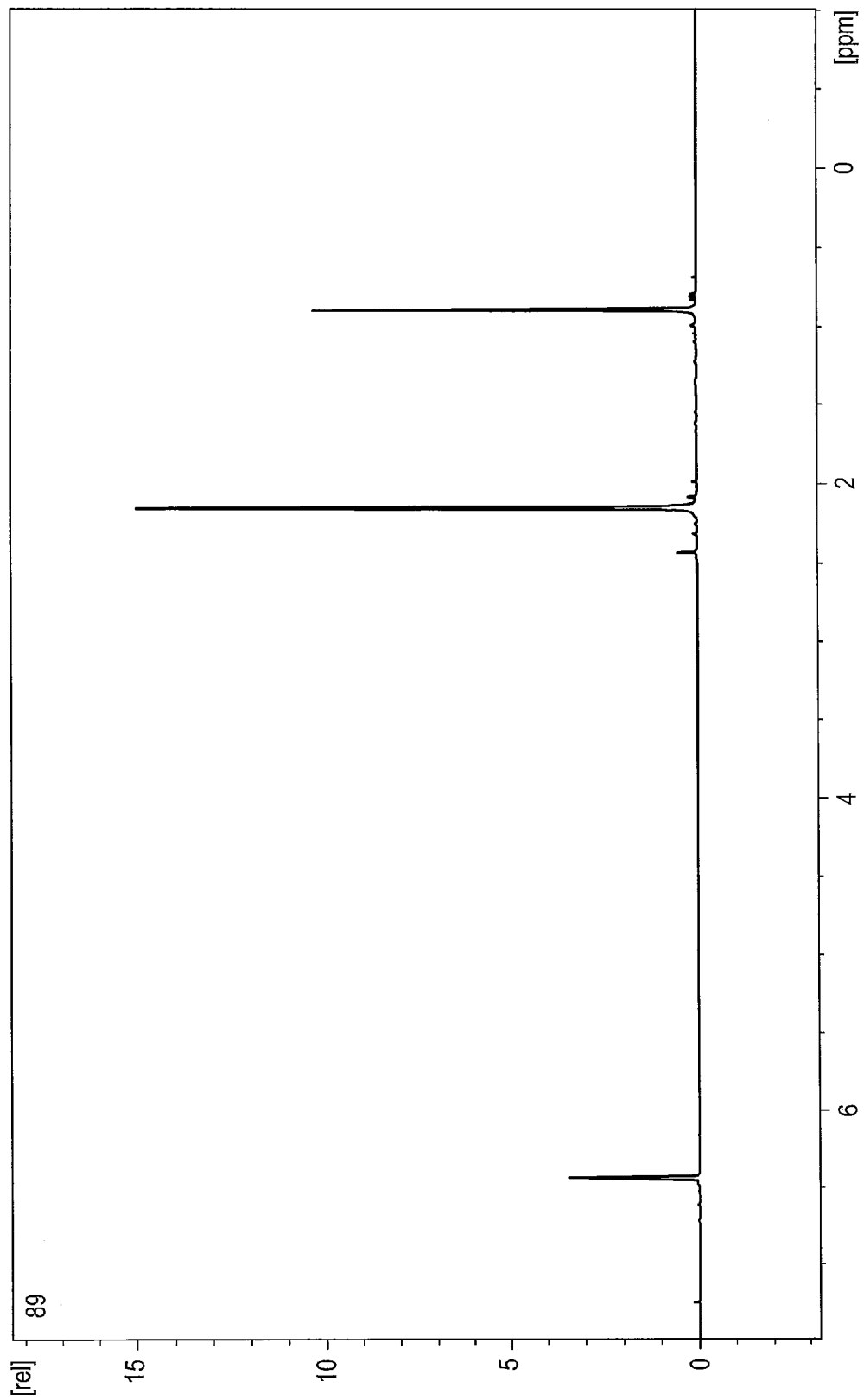
FIG. 2 is $^1$H-NMR spectra of liquids trapped using 1-MCP precursors obtained in Example 1 in Experimental Example 1.
Figure 3:
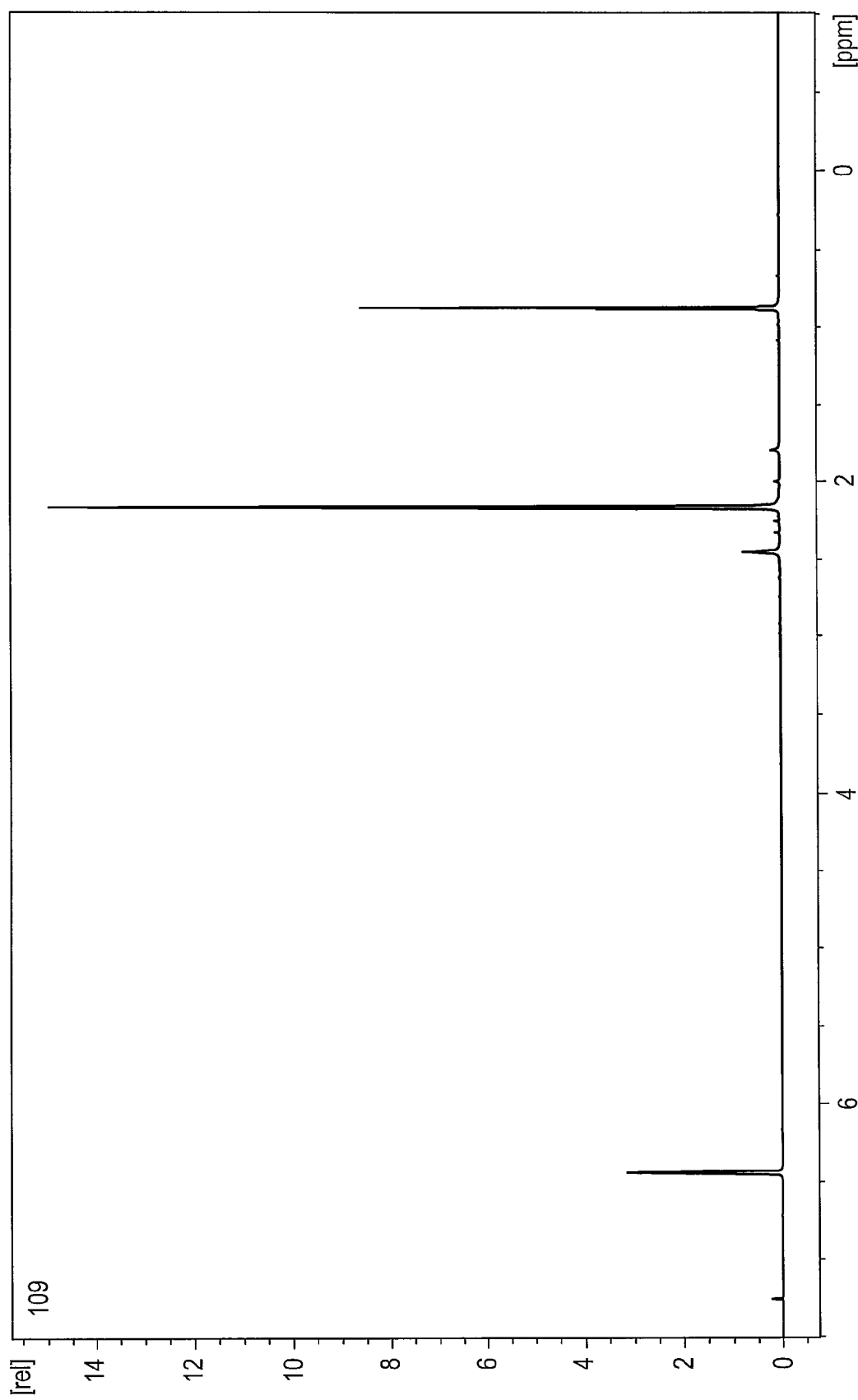
FIG. 3 is $^1$H-NMR spectra of liquids trapped using 1-MCP precursors obtained in Example 6 in Experimental Example 1.

Compared with FIGS. 1 through 3, the differences between them can be readily seen. That is, peaks plotted at δ=−0.3 to +0.5 in $^1$H-NMR spectra of FIG. 1 (represented by an oval) are not observed in FIGS. 2 and 3. These peaks plotted at δ=−0.3 to +0.5 correspond to fluorotrimethylsilane (b.p. 16° C./1 atm) obtained as byproducts in the process for preparing 1-MCP by the reaction of 1-methyl-1-(methanesulfonyloxy)-2-(trimethylsilyl)cyclopropane with fluoride ions (F$^−$), and to hexamethyldisiloxane modified by reaction of the fluorotrimethylsilane with water. On the other hand, when 1-methyl-1-(methanesulfonyloxy)-2-(dimethylbutylsilyl)cyclopropane or 1-methyl-1-(methanesulfonyloxy)-2-(dimethylphenylsilyl)cyclopropane reacts with fluoride ions (F$^−$) to produce 1-MCP, the corresponding byproducts were not observed. This indicates that volatile byproducts were not discharged from the container to the outside. As a result, like $^1$H-NMR spectra of FIGS. 2 and 3, no peak was observed at δ=−0.3 to +0.5.

Results of $^1$H-NMR for 1-MCP are as follows.

$^1$H-NMR (CDCl$_3$, δ): 6.447 (1H, s, 1-MCP), 1.154 (3H, s, 1-MCP), 0.896 (2H, s, 1-MCP).

Results of $^1$H-NMR for fluorotrimethylsilane and hexamethylsiloxane are as follows.

$^1$H-NMR (CDCl$_3$, δ): 0.253 (doublet, J=7.4 Hz, Long range coupling of F—SiMe$_3$).

$^1$H-NMR (CDCl$_3$, δ): 0.1556 (singlet, Me$_3$SiOSiMe$_3$).

Experimental Example 2

F-Detection by Ion Chromatography and Comparison of Release of Fluoride Compounds Three 1-MCP precursors, 1-methyl-1-(methanesulfonyloxy)-2-(trimethylsilyl)cyclopropane, 1-methyl-1-(methanesulfonyloxy)-2-(dimethylbutylsilyl)cyclopropane, and 1-methyl-1-(methanesulfonyloxy)-2-(dimethylphenylsilyl) cyclopropane prepared in Comparative Example 1, Example 3 and Example 6 were used in an amount of 2.2 g (0.010 mol), 2.3 g (0.010 mol), 2.4 g (0.010 mol), respectively, to prepare 1-MCP in accordance with the same method as in Experimental Example 1, and a round bottom flak was purged with nitrogen to induce release of bubbles from the round flask to the outside. The gases thus discharged were continuously passed through two F$^−$-absorption tubes using 50 ml of distilled water over 30 minutes to trap F$^−$. An F-concentration for the aqueous solution thus trapped was measured by ion chromatography and compared with 0.5 ppm F$^−$ standard solution to calculate a concentration of trapped in the adsorption tube. The results thus obtained are shown in Table 1 below.

TABLE 1

| 1-MCP precursor | F⁻ adsorption tube 1 | F⁻ adsorption tube 2 |
|---|---|---|
| Trimethyl derivative | 132 ppm | 63 ppm |
| Butyldimethyl derivative | 0.12 ppm | 0.06 ppm |
| Phenyldimethyl derivative | 0.09 ppm | 0.05 ppm |

As can be seen from the results of detection of fluoride ions ($F^-$) in Table 1, when 1-MCP is prepared from 1-methyl-1-(methanesulfonyloxy)-2-(dimethylbutylsilyl)cyclopropane or 1-methyl-1-(methanesulfonyloxy)-2-(dimethylphenylsilyl)cyclopropane, unlike 1-methyl-1-(methanesulfonyloxy)-2-(trimethylsilyl)cyclopropane, fluoride-containing harmful volatile byproducts such as HF or fluorotrimethylsilane ($Me_3SiF$) were not substantially released.

As apparent from the above description, according to the present invention, 1-methylcyclopropene (1-MCP) can be directly prepared in situ using a certain 1-MCP precursor without generating highly volatile harmful by-products, fluorosilane (e.g., fluorotrimethylsilane). Accordingly, 1-MCP which effectively inhibits the action of ethylene of accelerating the ripening process of agricultural products including fruits, flowers and vegetables can be prepared in a simple manner and then directly applied to plants without any separation process of a harmful volatile byproduct. Thus, the use of the method of the present invention enables preparation of 1-MCP in situ in a farmhouse or agriculture storage space and thus convenient application of the 1-MCP to plants, to thereby considerably improve storage stability of agricultural products.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for directly preparing 1-methylcyclopropene (1-MCP) which inhibits the action of ethylene of accelerating the ripening process of plants, which comprises
reacting a predetermined 1-methylcyclopropene precursor of Formula 2 or 3 with a base or fluoride anion material, and applying the 1-methylcyclopropene to plants:

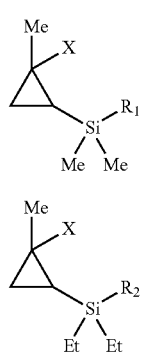

wherein
Me is methyl;
Et is ethyl;
$R_1$ is substituted or unsubstituted $C_2$-$C_{10}$ alkyl or $C_6$-$C_{10}$ aryl;
$R_2$ is substituted or unsubstituted $C_1$-$C_{10}$ alkyl or $C_6$-$C_{10}$ aryl; and
X is $OSO_2T$, in which T is substituted or unsubstituted $C_1$-$C_{10}$ alkyl or $C_6$-$C_{10}$ aryl.

2. The method according to claim 1, wherein the application of the 1-MCP to plants is carried out by gas releasing process.

3. The method according to claim 1, wherein
$R_1$ is selected from ethyl, propyl, butyl, isobutyl, pentyl, hexyl, octyl, phenyl, toluoyl, methoxyphenyl and 3-methoxypropyl;
$R_2$ is selected from methyl, ethyl, propyl, butyl, isobutyl, pentyl and hexyl; and
X is selected from methanesulfonyloxy, ethanesulfonyloxy, propanesulfonyloxy, butanesulfonyloxy, isopropanesulfonyloxy, benzenesulfonyloxy, and toluenesulfonyloxy.

4. The method according to claim 3, wherein $R_1$ is $C_2$-$C_8$ alkyl or $C_6$-$C_8$ aryl.

5. The method according to claim 3, wherein $R_2$ is methyl.

6. The method according to claim 1, wherein the 1-MCP precursor is 1-methyl-1-(methanesulfonyloxy)-2-(dimethylpropylsilyl)cyclopropane.

7. The method according to claim 1, wherein the 1-MCP precursor is 1-methyl-1-(methanesulfonyloxy)-2-(dimethylbutylsilyl)cyclopropane.

8. The method according to claim 1, wherein the 1-MCP precursor is 1-methyl-1-(methanesulfonyloxy)-2-(dimethylpentylsilyl)cyclopropane.

9. The method according to claim 1, wherein the 1-MCP precursor is 1-methyl-1-(methanesulfonyloxy)-2-(dimethylhexylsilyl)cyclopropane.

10. The method according to claim 1, wherein the 1-MCP precursor is 1-methyl-1-(methanesulfonyloxy)-2-(dimethylheptylsilyl)cyclopropane.

11. The method according to claim 1, wherein the 1-MCP precursor is 1-methyl-1-(methanesulfonyloxy)-2-(dimethyloctylsilyl)cyclopropane.

12. The method according to claim 1, wherein the 1-MCP precursor is 1-methyl-1-(methanesulfonyloxy)-2-(dimethylphenylsilyl)cyclopropane.

13. The method according to claim 1, wherein the 1-MCP precursor is 1-methyl-1-(methanesulfonyloxy)-2-(dimethyl-p-toluoylsilyl)cyclopropane.

14. The method according to claim 1, wherein the 1-MCP precursor is 1-methyl-1-(methanesulfonyloxy)-2-(diethylmethylsilyl)cyclopropane.

15. The method according to claim 1, wherein the fluoride anion material is tetraalkylammonium fluoride of Formula 4 below:

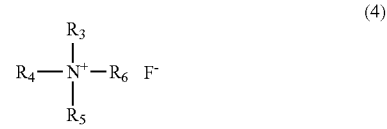

wherein $R_3$, $R_4$, $R_5$ and $R_6$ are each independently $C_1$-$C_{20}$ alkyl or $C_6$-$C_{10}$ aryl.

16. The method according to claim 1, wherein the 1-MCP precursor is the compound of Formula 2 and yields a by-product of fluorosilane represented by the following Formula 5 during the preparation of 1-MCP,
wherein the by-product absorbs neighboring water to produce a siloxane compound of Formula 6 below:

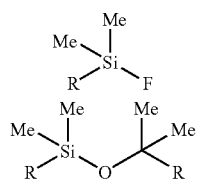
(5)

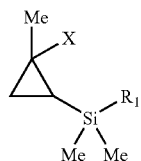
(6)

wherein R is as defined above for $R_1$.

17. A compound of the following Formula 2, useful as a 1-MCP precursor which reacts with a base or a fluoride anion material to synthesize 1-MCP:

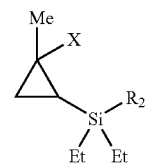
(2)

wherein Me is methyl;
$R_1$ is substituted or unsubstituted $C_2$-$C_{10}$ alkyl or $C_6$-$C_{10}$ aryl; and
X is $OSO_2T$, in which T is substituted or unsubstituted $C_1$-$C_{10}$ alkyl or $C_6$-$C_{10}$ aryl.

18. A compound of the following Formula 3, useful as a 1-MCP precursor which reacts with a base or a fluoride anion material to synthesize 1-MCP:

(3)

wherein Me is methyl;
Et is ethyl;
$R_2$ is substituted or unsubstituted $C_1$-$C_{10}$ alkyl or $C_6$-$C_{10}$ aryl; and
X is $OSO_2T$, in which T is substituted or unsubstituted $C_1$-$C_{10}$ alkyl or $C_6$-$C_{10}$ aryl.

* * * * *